United States Patent [19]

Kano et al.

[11] 3,967,950
[45] July 6, 1976

[54] COMBATING WEEDS IN RICE WITH BENZOTHIAZOLE DERIVATIVES

[75] Inventors: Saburo Kano; Osami Nomura, both of Odawara; Yoshihiko Hirono, Hiratsuka; Hisao Ishikawa, Oiso; Shozo Yamada, Hiratsuka, all of Japan

[73] Assignee: Nippon Soda Company Limited, Tokyo, Japan

[22] Filed: June 10, 1974

[21] Appl. No.: 477,930

[30] Foreign Application Priority Data

July 2, 1973  Japan.................................. 48-74610

[52] U.S. Cl.................................... 71/90; 260/305
[51] Int. Cl.$^2$............................................ A01N 9/22
[58] Field of Search.......................................... 71/90

[56] References Cited
UNITED STATES PATENTS

| | | |
|---|---|---|
| 2,756,135 | 7/1956 | Searle.................................... 71/90 |
| 3,714,177 | 1/1973 | Engelhart............................ 71/90 X |
| 3,818,024 | 6/1974 | Krenzer................................ 71/90 X |
| 3,845,069 | 10/1974 | Schafer et al........................ 71/90 X |

*Primary Examiner*—Lewis Gotts
*Assistant Examiner*—Catherine L. Mills
*Attorney, Agent, or Firm*—George B. Oujevolk

[57] ABSTRACT

Benzothiazole derivatives of the general formula:

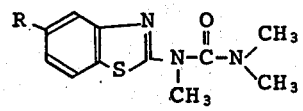

wherein R is chlorine atom, alkyl having from 1 to 4 carbon atoms or methoxy; are useful as selective herbicide.

3 Claims, No Drawings

COMBATING WEEDS IN RICE WITH BENZOTHIAZOLE DERIVATIVES

DETAILED DESCRIPTION OF THE INVENTION

The present invention relates to 3-(5-substituted benzothiazole-2-yl)-1,1,3-trimethylurea, their method of preparation, and the use thereof as a selective herbicide.

The compounds of the invention may be represented by the formula:

(1) 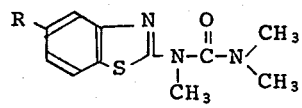

wherein R is chlorine atom, alkyl having from 1 to 4 carbon atoms or methoxy.

Hitherto, it is said in U.S. Pat. No. 2,756,135 that 3-(2-benzothiazolyl)-1,1,3-trimethylurea having herbicidal activity can be prepared by reaction of a 2-methylaminobenzothiazole with a N,N-dimethylcarbamoylchloride as illustrated by the following equation:

(2) 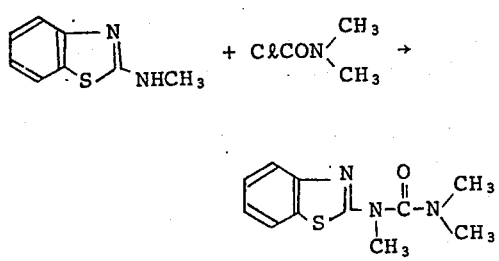

however, said compound was not obtained, but starting materials were recovered though the inventor followed the above reaction according to the Example 1 and 3 of the specification of U.S. Pat. No. 2,756,135.

In case of using a 2-methylamino-5-substituted benzothiazole instead of a 2-methylaminobenzothiazole, starting materials were recovered and objective product was not obtained. As the results of a lot of experiments, it has been found that the compound of this invention can be prepared be the reactions illustrated below:

In practical method of the reaction described in above (1), 2-methylamino-5-substituted benzothiazole and N,N-dimethylcarbamoylchloride are dissolved in an inert solvent and sodiumhydrid is added dropwise to the mixture which is stirred, preferably in a stream of nitrogen.

As an inert solvent, benzene, toluene, tetrahydrofuran, dimethylformamide and dimethylsulfoxide etc. are used. Ordinarily, temperatures from the range of $-10 \sim 20°C$, and preferably $-5 \sim 20°C$ are satisfactorily employed.

After the end of the reaction, the reaction mixture may be poured into water and the precipitate is separated from an aqueous solution by filtration or from an extraction by solvent.

The separated compound may be further washed with water, if necessary, and purified by recrystallizing from an organic solvent or by column chromatography.

In case of the reaction described in above (2), 2-methylamino-5-substituted benzothiazole is allowed to react with phosgene in the presence of $(C_2H_5)_2O \cdot BF_3$ using an organic solvent such as benzene, toluene and ether etc. at a temperature from $-20°$ to $70°$, preferably $-10°$ to $50°C$, and at this time N-methyl-N-(5-substituted benzothiazole-2-yl)carbamic acid chloride as intermediates is prepared. Then, dimethylamine is added to the reaction mixture and 3-(5-substituted benzothiazole-2-yl)-1,1,3-trimethylurea is obtained by the same post-treatment as the above (1).

The oily compound in the present invention is isolated as hydrogen chloride salt by blowing dry hydrogen chloride into said oily compound in an organic solvent.

The product is identified by means of an elementary analysis, NMR spectrum and IR spectrum.

The methods of preparing typical compounds of the present invention is illustrated by the following examples.

EXAMPLE 1

3-(5-chlorobenzothiazole-2-yl)-1,1,3-trimethylurea

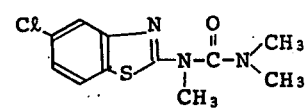

N,N-dimethylcarbamoylchloride (1.1g) and 5-chloro-2-methylaminobenzothiazole (2g) were dissolved in dimethylformamide (25ml) and the mixture was stirred while adding slowly sodiumhydride (0.44g, (3) 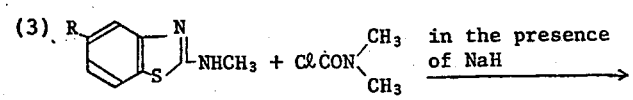

(4) 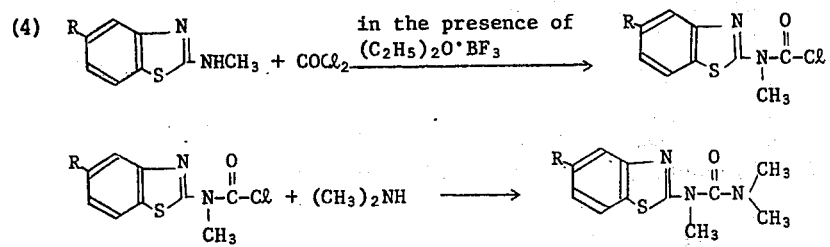

55% oily) in a stream of nitrogen for an hour and maintaining the temperature below −5°C. After stirring 3 additional hours at the room temperature, the mixture was poured into water (100ml) and the precipitate was filtrated, washed and dried.

White needles (1.7g) having a melting point of 115°–117°C was obtained by recrystallizing from ligroin.

Analysis. Calculated for $C_{11}H_{12}N_3OSCl$ (%) : C, 48.98; H, 4.45; N, 15.58; Cl, 13.17. Found (%) : C, 48.70; H, 4.30; N, 15.84; Cl, 12.91.

EXAMPLE 2

3-(5-methylbenzothiazole-2-yl)-1,1,3-trimethylurea

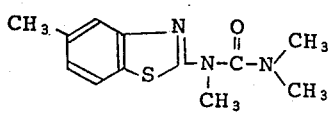

$(C_2H_5)_2O·BF_3$ (0.9g) was added dropwise to toluene (110ml) in which plosgene (5g) were dissolved, 5-methyl-2-methylaminobenzothiazole (7.5g) were added to the mixture and it was stirring 3 hours at 60°C. The mixture was cooled below 10°C after maintained the temperature 70°C for an hour and dimethylamine (4g) was added to it maintaining the temperature below 30°C.

After stirring an hour at the temperature from the range of 25° to 30°C the precipitate (hydrochloric acid salt of dimethylamine) was filtered and white crystal was obtained by concentrating toluene solution under reduced pressure.

White needles (4.2g) having a melting point of 72-74°C were obtained by recrystallizing from ligroin.

Analysis. Calculated for $C_{12}H_{15}N_3OS$ (%): C, 57,83; H, 6.02; N, 16.87. Found (%): C, 57.88; H, 6.10; N, 16.89.

EXAMPLE 3

3-(5-ethylbenzothiazole-2-yl)-1,1,3-trimethylurea

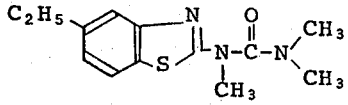

N,N-dimethylcarbamoylchloride (0.9g) and 5-ethyl-2-methylaminobenzothiazole (1.6g) were dissolved in dimethylformamide (20ml) and the mixture was stirred while adding slowly sodium-hydride (0.36g, 55% oily) in a stream of nitrogen for an hour and maintained the temperature below −5°C. After stirring 3 additional hours, the mixture was poured into water (100ml) and oily substances having thin yellow color was obtained.

After the oily substances were extracted with chloroform and dried with magnesium sulfate, thin yellow oily substances (1.0g) having a refractive index of $n_D^{20} 1.6061$ was obtained from distillating chloroform under reduced pressure. It indicated an absorption of carbonyl group at a wavelength of 1670cm$^{-1}$ in IR spectrum. The hydrochloric acid salt of it having a melting point of 164°–166°C and a white color was obtained by blowing dry hydrogen chloride gas into oily substance.

Analysis of hydrochloride — Calculated for $C_{13}H_{18}N_3OSCl$ (%): C, 52.09; H, 5.99; N, 14.00; Cl, 11.83. Found (%): C, 52.20; H, 6.12; N, 14.23; Cl, 12.12.

EXAMPLE 4

3-(5-isopropylbenzothiazole-2-yl)-1,1,3-trimethylurea

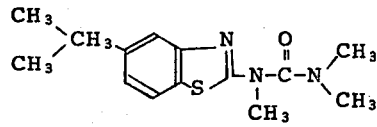

Phosgene (3.3g) were dissolved in toluene (100ml) and $(C_2H_5)_2O·BF_3$ (0.5g) was added dropwise to the mixture below −10°C.

Further, 5-isopropyl-2-methylaminobenzothiazole (4g) were added to the mixture and it was stirred for 3 hours at 60°C.

After maintaining it an hour at 70°C, the mixture was cooled below 10°C and dimethylamine (2g was added to it below 30°C. The resulting precipitate was removed by filtration after stirring an hour at the temperature of 25°–30°C and thin yellow oily substances (3g) were obtained by concentrating the toluene solution under reduced pressure.

White hydrochloric acid salt having a melting point of 135°–138°C was obtained by blowing dry hydrochloric acid gas into the oily substances in chloroform. It indicated an absorption of carbonyl group at a wavelength of 1665cm$^{-1}$ in IR spectrum.

Analysis of hydrochloride — Calculated for $C_{14}H_{20}N_3OSCl$ (%): C, 53.59; H, 6.38; N, 13.40; Cl 11.32.

Found (%) C, 53.17; H, 6.56; N, 13.14; Cl, 11.45.

EXAMPLE 5

3-(5-t-butylbenzothiazole-2-yl)-1,1,3-trimethylurea

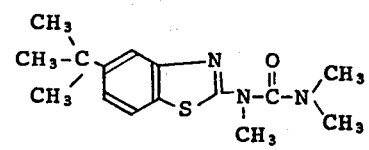

The same reaction procedures as Example 1 were carried out by using N,N-dimethylcarbamoylchloride (1.1g), 2-methylamino-5-t-butylbenzothiazole (2.2g) and sodiumhydride (0.44g, 55% oily), and thereby 3-(5-t-butylbenzothiazole-2-il)-1,1,3-trimethylurea having a melting point of 107° – 108°C was obtained as a white needles.

Analysis. Calculated for $C_{12}H_{15}N_3O_2S$ (%): C, 61.85; H, 7.21; N, 14.43. Found (%): C, 61.92; H, 7.18; N, 14.51.

EXAMPLE 6

3-(5-methoxybenzothiazole-2-yl)-1,1,3-trimethylurea

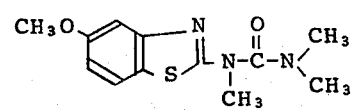

The same reaction procedures as Example 3 were carried out by using N,N-dimethylcarbamoylchloride (1,7g), 5-methoxy-2-methylaminobenzothiazole (3g) and sodiumhydride (0.68g, 55% oily), and thereby 3-(5-methoxybenzothiazole-2-yl)-1,1,3-trimethylurea (1.2g) having a refractive index of $n_D^{20}1.6098$ was obtained as a thin yellow oily substance and indicated an absorption of carbonyl group at a wavelength of 1660cm[116 1] in IR spectrum.

Analysis. Calculated for $C_{12}H_{15}N_3O_2S$ (%): C, 54.34; H, 5.66; N, 15.84. Found (%): C, 54.40; H, 5.70; N, 15.95.

EXAMPLE 7

3-(5-butylbenzothiazol-2-yl)-1,1,3-trimethylurea

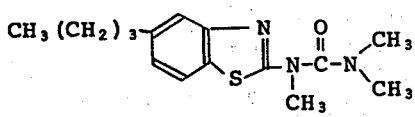

The same reaction procedures as Example 3 were carried out by using N,N-dimethylcarbamoylchloride (1.7g), 5-butyl-2-methylaminobenzothiazole (3.3g) and sodiumhydride (0.75g, 50%), and thereby 3-(5-butylbenzothiazol-2-yl)-1,1,3-trimethylurea having a refractive index of $n_D^{17}1.5820$ was obtained as oily substance.

It is already know that 3-(2-benzothiazolyl)-1,1,3-trimethylurea has strong herbicidal properties as shown in U.S. Pat. No. 2,756,135. It exhibits selective herbicidal properties when it is used in cotton, wheat and barley cultivation, however it cannot be used for selective weed control in rice cultivation because it has strong herbicidal activity in soil treatment and phytotoxicity for rice plant. Moreover, when it is applied after emergence in wheat cultivation, in which the weeds have already grown to a substantial height, it is difficult to perfectly control such weeds without damage to the cultivated plants.

And it has been disclosed in German Offenlegungsschrift P 2150107.5 that 1,3-dimethyl-1-[2-(5-methylbenzothiazolyl)]-urea is highly selective in wheat cultivation and kills only weeds, even when both the weeds and wheat have grown. But it cannot be used in rice cultivation because there is heavy phytotoxicity to rice plant the same as 3-(2-benzothiazolyl)-1,1,3-trimethylurea.

The inventors synthesized various benzothiazolylureas and examined the herbicidal activity thereof, and have discovered that 3-(2-benzothiazolyl)-1,1,3-trimethylurea having at 5 position of benzothiazol ring a substituent such as chlorine, methyl, ethyl, isopropyl or tert-butyl group is very suitable for selective weed control in both rice and wheat cultivation, particularly methyl ethyl, and tert-butyl substituents are superior.

Namely, the compound of the present invention hardly damage rice plant and wheat, whereas it completely destroys many kind of weeds such as smooth pigweed (*Chenopodium album* L.), green foxtail (*Panicum viride* L.), monochoria (*Monochoria vaginalis* PRESL), common purslane (*Portulaca oleracea* L.), common sow thistle (*Sonchus oleraceus* L.), common chickweed (*Alsine media* L.), nutgrass (*Cyperus ratundus* L.), barnyard grass (*Echinochloa oryzicola* VASING.) and large crab-grass (*Panicum sanguinalis* L.) by foliar and soil treatments.

Consequently, the compounds of the present invention can be used for controlling weeds not only in wheat cultivation, but also in rice cultivation, because there is no fear for phytotoxicity to rice plant and wheat.

It is another advantage that the compounds of the present invention have low toxicity for warm blooded animals and fish.

In this invention, it is desirable that a proper quantity of active ingredient more than 50g per 10 are, preferably 50 – 200g per 10 are ("are" is "100 square meters"), is selectively used in accordance with the kind of composition. The compound may be applied to the plants or soils as it is or as wettable powder, emulsifiable concentrate, dust formulation, granular formulation or others in a form generally used in pesticidal compositions which is made by mixing with suitable carriers. As solid carriers, talc, bentonite, clay, diatomaceous earth, vermiculite, etc. are used. As liquid carriers, water, alcohol, benzene, xylene, cyclohexane, cyclohexanone, kerosine, dimethylformamide, dimethylsulfoxide etc. are used. Incidentally, wettable powder or emulsifiable concentrate containing proper quantity of the active compound is suspended or emulsified in water and then sprayed to the foliages of the weeds or to the soil around the cultivated plants. Furthermore, the compounds may be used as a mixture with the known herbicides such as triazine derivatives, thiolcarbamate derivatives and the others.

Some examples in this invention are stated below. But the main compounds and the additives are not defined limitedly by these Examples.

Example 8

| Wettable Powder | Parts by weight |
| --- | --- |
| 3-(5-chlorobenzothiazole-2-yl)-1,1,3-trimethylurea | 50 |
| Sodium alkylsulfonate | 8 |
| Diatomaceous earth | 32 |
| Silicic acid | 10 |

These are mixed homogeneously and micronized to fine particles. Consequently, wettable powder containing 50% of the active ingredient is obtained. In practical use, it is diluted to a certain concentration with water and is sprayed as a suspension.

Example 9

| Emulsifiable Concentrate | Part by weight |
| --- | --- |
| 3-(5-ethylbenzothiazole-2-yl)-1,1,3-trimethylurea | 30 |
| Polyoxyethylenealkylarylether | 8 |
| Xylene | 42 |
| Dimethylformamide | 20 |

These are mixed and dissolved. Consequently, emulsifiable concentration containing 30% of the active ingredient is obtained. In practical use, it is diluted to certain concentration with water and then is sprayed as an emulsion.

Example 10

| Dust Formulation | Part by weight |
| --- | --- |
| 3-(5-methylbenzothiazole-2-yl)-1,1,3-trimethylurea | 7 |
| Talc | 39 |
| Clay | 39 |

Example 10-continued

| Dust Formulation | Part by weight |
|---|---|
| Bentonite | 10 |
| Sodium alkylsulfate | 5 |

These are mixed homogeneously, reduced to fine particles. Consequently, dust formulation containing 7% of the active ingredient is obtained. In practical use, it is directly applied.

The compound of the present invention possess selective herbicidal activity and it must be stressed that the compounds of the above-mentioned general formula (1) in which R is methyl, ethyl or tert-butyl group particularly superior activity.

The superior selective herbicidal effect of compounds of this invention are clearly illustrated by the following tests.

TEST 1

Soil was packed in depth of 1cm in a dish having 9cm of diameter and 6cm of depth, and 15 seeds of rice plant and 40 seeds of barnyard grass were sown in it and covered slightly with soil. Said pot was filled with water when the test plants were grown to first leaf-stage.

Then, emulsifiable concentrate prepared by Example 9 were applied to the surface of the soil.

After 14 days, the degrees of damage to the test plants were observed and estimated by the value 0–5 which have the following meaning.

0: no effect
1: a few slightly burnt spots
2: marked damage to leaves
3: some leaves and parts of stalks partially dead
4: plant partially destroyed
5: plant completely destroyed or no germination The results were shown in Table 1.

Table 1

| Test compound | Application rate (g/10 are) | Growth state barnyard grass | rice plant |
|---|---|---|---|
| Cl-benzothiazole-N(CH₃)-C(O)-N(CH₃)₂ | 500 | 4 | 1 |
| | 250 | 3 | 0 |
| CH₃-benzothiazole-N(CH₃)-C(O)-N(CH₃)₂ | 500 | 5 | 0 |
| | 250 | 5 | 0 |
| C₂H₅-benzothiazole-N(CH₃)-C(O)-N(CH₃)₂ | 500 | 5 | 0 |
| | 250 | 4 | 0 |
| (CH₃)₂CH-benzothiazole-N(CH₃)-C(O)-N(CH₃)₂ | 500 | 5 | 1 |
| | 250 | 5 | 1 |
| CH₃O-benzothiazole-N(CH₃)-C(O)-N(CH₃)₂ | 500 | 5 | 0 |
| | 250 | 4 | 0 |
| (CH₃)₃C-benzothiazole-N(CH₃)-C(O)-N(CH₃)₂ | 500 | 4 | 1 |
| | 250 | 3 | 0 |
| CH₃(CH₂)₃-benzothiazole-N(CH₃)-C(O)-N(CH₃)₂ | 500 | 5 | 0 |
| | 250 | 5 | 0 |
| Comparative compound * benzothiazole-N(CH₃)-C(O)-NHCH₃ | 500 | 4 | 4 |
| | 250 | 3 | 2 |
| * benzothiazole-N(CH₃)-C(O)-N(CH₃)₂ | 500 | 5 | 5 |
| | 250 | 5 | 2 |

Table 1-continued

| Test compound | Application rate (g/10 are) | Growth state barnyard grass | rice plant |
|---|---|---|---|
| 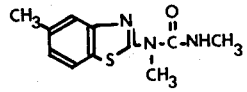 ** | 500 | 5 | 4 |
|  | 250 | 3 | 3 |

\* U.S.P. 2,756,135
\*\* Offenlegungsschrift P 2150107.5

TEST 2

Soil was packed in a dish having 9cm of diameter and 6cm of depth and 50 seeds of monochoria were sown in it.

An emulsifiable concentrate prepared by the similar method of Example 9 was diluted with water to a specified concentration and was sprayed on it when monochoria were grown to the first-leaf stage (height : 1cm).

After 7 and 20 days, a growth states of the test plants were observed and estimated by the value of 0–5 which have the same meanings of those of Test 1.

The results were shown in the Table 2.

Table 2

| Test compound | Application rate (g/10 are) | Growth state 7 days | 20 days |
|---|---|---|---|
| 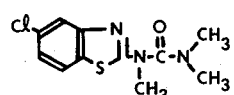 | 200 | 0 | 5 |
|  | 100 | 0 | 3 |
| 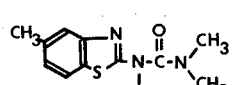 | 200 | 1 | 5 |
|  | 100 | 1 | 5 |
| 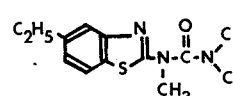 | 200 | 2 | 5 |
|  | 100 | 2 | 5 |
| 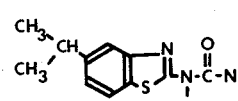 | 200 | 4 | 5 |
|  | 100 | 4 | 5 |
| 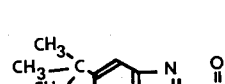 | 200 | 4 | 5 |
|  | 100 | 4 | 5 |
| 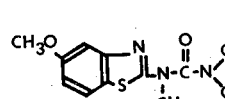 | 200 | 2 | 5 |
|  | 100 | 2 | 5 |
| Comparative compound 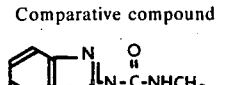 \* | 200 | 0 | 2 |
|  | 100 | 0 | 0 |
| 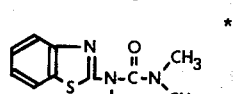 \* | 200 | 0 | 0 |
|  | 100 | 0 | 0 |

Table 2-continued

| Test compound | Application rate (g/10 are) | Growth state | |
|---|---|---|---|
| | | 7 days | 20 days |
| 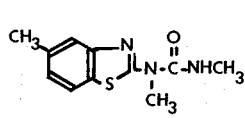 ** | 200 | 2 | 4 |
| | 100 | 0 | 2 |

\* U.S.P. 2,756,135
\*\* Offenlegungsschrift P 2150107.5

TEST 3

About 10 seeds of wheat were sown in a flower-pot and covered slightly with soil containing the seeds of annual bluegrass.

An emulsifiable concentrate prepared by the similar method of Example 9 was diluted with water to a specified concentration and was sprayed on them when wheat and annual bluegrass were grown to the 6th-leaf stage.

After 21 days from the spraying, the growth states of the plants were observed and estimated by the value of 0–5 which have the same meanings of those of Test 1. The results were shown in the Table 3.

TEST 4

Soil was packed in a pot of 100cm², 10 seeds of wheat were sown in it and covered slightly with soil containing the seeds of large crab-grass and smooth pigweed.

An emulsifiable concentrate prepared by the similar method of Example 9 was diluted with water to a specified concentration and was sprayed on the soil next day, then the pot was put into a green-house.

After 21 days from the spraying, the growth states of the plants were observed and estimated by the value of 0–5 which have the same meanings of those of Test 1.

The results were shown in Table 4.

Table 3

| Test compound | Application rate (g/10 are) | Growth state | |
|---|---|---|---|
| | | wheat | annual bluegrass |
| 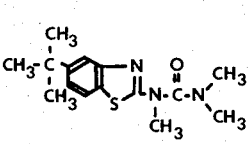 | 50 | 0 | 4 |
| | 100 | 0 | 5 |
| | 200 | 0 | 5 |
| 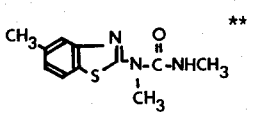 ** | 50 | 0 | 1 |
| | 100 | 0 | 1 |
| | 200 | 0 | 2 |
| Untreated | — | 0 | 0 |

Table 4

| Test compound | Application rate (g/10 are) | Growth states | | |
|---|---|---|---|---|
| | | wheat | large crab-grass | smooth pigweed |
| 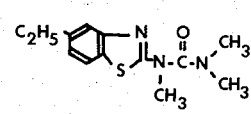 | 125 | 0 | 2 | 3 |
| | 250 | 0 | 3 | 4 |
| 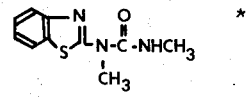 * | 125 | 0 | 0 | 0 |
| | 250 | 0 | 0 | 2 |
| 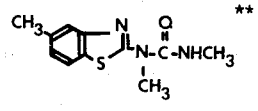 ** | 125 | 0 | 0 | 1 |
| | 250 | 0 | 0 | 3 |
| Untreated | — | 0 | 0 | 0 |

We claim:
1. A method of combating weeds in rice cultivation which comprises applying to the weed habitat a herbicidally effective amount of 3-(5-methylbenzothiazole-2-il)-1,1,3-trimethylurea.
2. A method of combating weeds in rice cultivation which comprises applying to the weed habitat a herbicidally effective amount of 3-(5-ethylbenzothiazole-2-il)-1,1,3-trimethylurea.
3. A method of combating weeds in rice cultivation which comprises applying to the weed habitat a herbicidally effective amount of 3-(5-tert-butylbenzothiazole-2-il)-1,1,3-trimethylurea.

* * * * *